United States Patent
Beck et al.

(10) Patent No.: US 10,357,195 B2
(45) Date of Patent: Jul. 23, 2019

(54) PUPILLOMETRY AND SENSOR FUSION FOR MONITORING AND PREDICTING A VEHICLE OPERATOR'S CONDITION

(71) Applicant: Panasonic Intellectual Property Management Co., Ltd., Osaka (JP)

(72) Inventors: Ariel Beck, Singapore (SG); Khai Jun Kek, Batu Pahat (MY)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/666,017

(22) Filed: Aug. 1, 2017

(65) Prior Publication Data
US 2019/0038204 A1   Feb. 7, 2019

(51) Int. Cl.
*A61B 5/18* (2006.01)
*B60W 40/08* (2012.01)
(Continued)

(52) U.S. Cl.
CPC .............. *A61B 5/18* (2013.01); *A61B 5/024* (2013.01); *A61B 5/1172* (2013.01);
(Continued)

(58) Field of Classification Search
CPC ....... A61B 5/18; A61B 5/7275; A61B 5/1176; A61B 5/024; A61B 5/163; A61B 5/1172; B60W 40/08; B60W 2040/0818
See application file for complete search history.

(56) References Cited

U.S. PATENT DOCUMENTS

| 7,438,418 B2 | 10/2008 | Marshall |
| 8,981,942 B2 | 3/2015 | He et al. |

(Continued)

FOREIGN PATENT DOCUMENTS

WO   2014/027933   2/2014

OTHER PUBLICATIONS

Tianchi Liu et al., "Driver distraction detection using semi-supervised machine learning", IEEE Transactions on Intelligent Transportation Systems vol. 17, No. 4, 2016, pp. 1108-1120.
(Continued)

*Primary Examiner* — Brian Wilson
(74) *Attorney, Agent, or Firm* — McDermott Will & Emery, LLP

(57) ABSTRACT

A system and method for monitoring the condition of the driver of a vehicle including both the level of distraction being experienced by him/her as well his/her cardiac health are described. The system can detect and predict behavioral and cognitive distraction in real time. It can also monitor a driver's physical condition, detect and predict health events such as a myocardial infarction. The system can fuse inputs from various sensors and components including vehicle information (through CAN networks or other), IR camera, heart rate sensors, eye tracking and pupillometry technology. The distraction detection and health monitoring can be done in separate modules. Fusion algorithms can detect and predict risk related to the driver's lack of attention and the likelihood that he/she is or will experience a cardiac event.

27 Claims, 4 Drawing Sheets

(51) Int. Cl.
  *A61B 5/16* (2006.01)
  *A61B 5/024* (2006.01)
  *A61B 5/1172* (2016.01)
  *A61B 5/1171* (2016.01)
  *A61B 5/00* (2006.01)

(52) U.S. Cl.
  CPC ............ *A61B 5/1176* (2013.01); *A61B 5/163* (2017.08); *A61B 5/7275* (2013.01); *B60W 40/08* (2013.01); *B60W 2040/0818* (2013.01)

(56) References Cited

U.S. PATENT DOCUMENTS

| | | | | |
|---|---|---|---|---|
| 9,135,803 | B1* | 9/2015 | Fields | B60K 28/066 |
| 9,440,657 | B1 | 9/2016 | Fields et al. | |
| 2012/0105234 | A1* | 5/2012 | Oguri | A61B 5/18 |
| | | | | 340/576 |
| 2013/0325202 | A1 | 12/2013 | Howard et al. | |
| 2014/0276090 | A1* | 9/2014 | Breed | A61B 5/18 |
| | | | | 600/473 |
| 2016/0253895 | A1* | 9/2016 | Prakah-Asante | |
| | | | | G08B 21/0453 |
| | | | | 340/539.12 |
| 2017/0355377 | A1* | 12/2017 | Vijaya Kumar | B60W 40/08 |

OTHER PUBLICATIONS

Yuan Liao et al., "Detection of driver cognitive distraction: A comparison study of stop-controlled intersection and speed-limited highway", IEEE Intelligent Transportation Systems vol. 17, No. 6, 2016, pp. 1628-1637.

Francesco Biondi et al., "Cognitive distraction impairs drivers' anticipatory glances: An on-road study", Driving assessment 2015: Int. Symp on Human Factors in Driver Assessment, Training, and Vehicle Design. Eds. D. V. McGehee, J. D. Lee, and M. Rizzo. Iowa City: Public Policy Center, Uni. of Iowa, 2015.

Jeff Klingner, "Measuring cognitive load during visual tasks by combining pupillometry and eye tracking", Diss. Stanford University, 2010.

Oskar Palinko et al., "Estimating cognitive load using remote eye tracking in a driving simulator", Proceedings of the 2010 symposium on eye-tracking research & applications, ACM, 2010.

\* cited by examiner

PUPILLOMETRY AND SENSOR FUSION FOR MONITORING AND PREDICTING A VEHICLE OPERATOR'S CONDITION

TECHNICAL FIELD

A system and method to predict and monitor the condition of the driver of a motor vehicle is described.

BACKGROUND

Motor vehicle accidents account for thousands of deaths and injuries each year. In the United States, traffic collision related deaths exceeded 35,000 in 2015. Worldwide, the estimated annual number of deaths from motor vehicle collisions has exceeded 1,000,000 in recent years. Moreover, collisions cause injury and disability as well as financial costs to both the individuals involved and society.

A number of factors contribute to the risk of collision, including vehicle design, speed of operation, road design, environment, impairment due to alcohol or drugs, and driver skill/behavior. Studies of crash data have found that driver error, intoxication and other human factors contribute wholly or partly to as much as 93% of crashes.

Driver health, in particular, cardiac events such as Sudden Cardiac Death (SCD) leads to a significant number of vehicle accidents each year. Heart disease is rampant in industrialized nations and the number of heart attacks experienced while driving has increased in recent years. Heart disease is the most common cause of natural death in the U.S. and many other industrialized countries. Further, people are spending more time driving and often drive well into their elder years. These factors have led to an increase in the number of accidents that result from cardiac events such as myocardial infarction.

Driver distraction is also attributed to a significant percentage of motor vehicle accidents each year. When distracted, a driver loses awareness of his/her driving situation which increases the risk of an accident as well as the distance needed to slow or stop. Recent studies found that distraction and inattention contribute to approximately 80% of crashes or near crashes. As a result, many jurisdictions have enacted laws banning the use of electronic devices such as smart phones while driving.

Distractions are often separated into three distinct groups: visual, manual, and cognitive. Visual distraction involves taking one's eyes off the road. Manual distraction, also referred to as biomechanical distraction, involves taking one's hands off the wheel. This might occur when a driver reaches for a cell phone or eats while driving. Cognitive distraction occurs when an one's focus is not directly on the act of driving. Cognitive distraction delays a driver's response to critical events. A fourth type of distraction, auditory distraction, may also be considered. Auditory distraction is caused when sounds prevent a driver from making the best use of his/her hearing. This occurs when, for example, a driver focuses his/her hearing toward a cell phone conversation. All distractions compromise the safety of the driver, passengers, bystanders and those in other vehicles Improvements in the design of motor vehicles have improved their safety, decreasing the number of fatalities and the severity of injuries in accidents. Modern automobiles typically undergo extensive crash testing to improve their safety. Further, vehicles are typically equipped with multiple air bags to protect occupants in case of an accident. Despite improvements in vehicle design and safety, motor vehicles lack any means of monitoring the status of the driver and his/her attention. Doing so could prevent many motor vehicle accidents and greatly reduce the number of vehicular injuries and deaths. Accordingly, there is a need for a system to monitor a driver's level of attention as well as his/her physical health.

Previous efforts have focused on driver observation in attempt to predict cognitive function. For example, U.S. Pat. No. 9,440,657 describes a system that monitors physiological activity of a driver. The data is analyzed by a computer or smart phone to predict whether a driver is impaired. The system relies on movement of the vehicle and driver to determine irregularities and activate an alert. Similarly, WO 2014/027933 describes a driver awareness detection arrangement that uses physiological data in conjunction with vehicle operation information to determine whether a driver is drowsy or impaired. The systems use conventional cameras to observe a driver and movement of an automobile. However, neither system can detect or predict levels of distraction or cardiac events that the driver may experience.

U.S. patent application Ser. No. 13/486,224 describes a driver state module for interfacing with a vehicle and its surroundings. It includes a frame memory for storing representations of behaviors and an evaluation system for ranking the frames based on goals and rewards. The system also uses conventional cameras and relies on driver behavior to predict driver attention and awareness. However, the system may not effectively detect or predict levels of driver distraction and it does not monitor a driver for cardiac events.

Other systems have demonstrated that eye movements can help gauge the level of distraction experienced by a driver. For example, U.S. Pat. No. 8,981,942 describes a system with an optical sensor that monitors a driver to detect eye blinks, head nods, head rotations, and/or gaze fixations. Another optical sensor can monitor the road ahead of the vehicle to detect lane deviation, movement within the lane and time to collision. The system utilizes the data to predict a driver's state of impairment. However, the system does not analyze the driver's pupil activity and has limited effective use.

Although, these systems and methods monitor some aspects of a driver's health and level of attention, they have shortcomings. Conventional systems cannot predict when a user will get distracted and allow for preventive measures. Further, conventional systems do not exploit advances in pupillometry and are prone to error as they do not effectively account for particular characteristics of an individual or stimuli that one may experience in a driving environment. Moreover, conventional systems are not capable of monitoring a driver's cardiac health and predicting cardiac events.

Accordingly, there is a need for an improved system that monitors the cardiac activity and cognitive function of the driver of a motor vehicle. It should incorporate sensors that effectively monitor a driver's heart, eyes and pupil activity to more accurately determine whether a person is overly distracted or having a cardiac event. It should also be capable of predicting whether a driver is likely to become distracted based on a driver's habits and past incidences. Further, the system should be capable of utilizing external data to predict whether a driver is likely to experience a cardiac event.

SUMMARY OF THE INVENTION

The present inventors recognize that there exists a need for a system and method to combine eye tracking and vital sensing for driver monitoring to detect and predict distraction and cardiac events. The system described herein can detect behavioral and cognitive distraction in real time. It can also monitor a driver's physical condition and detect health events such as a cardiac event. Further, the system can predict whether a driver is likely to become distracted or suffer a debilitating episode such as a cardiac event.

The following summary is provided to facilitate an understanding of some of the innovative features unique to the disclosed embodiment and is not intended to be a full description. A full appreciation of the various aspects of the embodiments disclosed herein can be gained by taking into consideration the entire specification, claims, drawings, and abstract as a whole.

We describe a driver monitoring system for monitoring a person operating a vehicle that includes an eye tracking system and one or more heart rate sensors. The system is configured to collect data related to the eye tracking system and heart rate sensors. The system is further configured to fuse the data to obtain a value for the person's level of distraction. The system can also be configured to predict whether the person is likely to become distracted. Data from the heart rate sensors can be fused with the value for the person's level of distraction to predict whether he/she is likely to have a debilitating episode that can affect his/her ability to safely operate the vehicle. The system can record baseline levels of activity from the eye tracking system and heart rate sensors of a person to detect aberrations. The eye tracking system can include pupillometry sensors and sensors to monitor eye activity/movement as well as eyelid activity/movement.

Additional sensors can be included to identify a person based on his/her physical characteristics such as his/her fingerprints, facial characteristics and/or iris patterns. Vehicle sensors can also be included to provide data related to the location, speed and movements of the vehicle. The system can be configured to detect and predict a debilitating episode wherein a person experiences a loss of consciousness or loss of cognitive function due to a seizure, stroke, syncope, diabetes, drugs or alcohol, fatigue or low blood pressure. The system can also be configured to detect and predict a cardiac event such as acute angina, myocardial infraction or cardiac arrest. It can trigger a response if it determines or predicts that a person is or is likely to experience a cardiac event or is distracted beyond a threshold.

The system can account for external factors that can affect pupillometry including at least one of external lighting, variation between individuals and the person's mood or emotions. It can also include face analysis sensors to detect the position of the person's head as well as his/her facial expressions.

We also describe a driver monitoring system for monitoring a person operating a vehicle comprising an eye tracking system and one or more heart rate sensors that includes a second/high level of fusion. Data can be collected from the eye tracking system and the heart rate sensors and fused using an algorithm to obtain a value for the person's level of distraction. The system can also be configured to collect data from the heart rate sensors and fuse it with the value for the person's level of distraction to predict if the person will experience a debilitating episode. The debilitating episode can be a cardiac event such as acute angina, myocardial infraction or cardiac arrest. The debilitating episode can also be one in which the person experiences a loss of consciousness or loss of cognitive function due to a seizure, stroke, syncope, diabetes, drugs or alcohol, fatigue or low blood pressure.

The system can be configured to trigger a response if the system determines that a person is or will likely experience a debilitating episode. The system can also be configured to record baseline levels of activity of a person to detect aberrations. The system can include clinical data to predict whether the person operating the vehicle is likely to suffer a cardiac event. Additional sensors can also be included to monitor the location, speed and movements of the vehicle. Further, face analysis sensors can detect the position of the person's head as well as his/her facial expressions.

We also describe a system for analyzing a person operating a vehicle comprising one or more computers programmed to perform operations including (1) receiving data relating to the person's eyes and pupils, (2) receiving data relating to the person's heart rate, (3) a first fusion of data to determine and/or predict whether the person is unfit to drive because he/she is becoming overly distracted and (4) a second fusion of data to detect and/or predict if the person will experience a debilitating episode that can affect his/her ability to safely operate the vehicle. The system can include the additional operations of receiving data relating to the position and movement of a person's head and body and receiving data relating to the person's facial expressions. Further, the system can include the additional operation of receiving data related to the location speed and/or movement of the vehicle. Further, the system can be configured to analyze the output from the first fusion of data and the second fusion of data to ascertain whether the determination/prediction of a debilitating condition was a false positive. The step of fusing the input can account for external factors that can affect the person's pupils such as external lighting, individual differences and the person's mood or emotions.

In a first embodiment, there is provided a driver monitoring method comprising:
providing an eye tracking system; and
providing one or more heart rate sensors,
collecting data from the eye tracking system and the one or more heart rate sensors and recording the data to establish baseline levels of activity for a person operating a vehicle;
fusing the data to determine the level of distraction being experienced by the person operating the vehicle; and
predicting whether the person operating the vehicle is likely to become distracted.

In the driver monitoring method of first embodiment, the method can further predict whether the person operating the vehicle will suffer a debilitating episode that can diminish his/her ability to safely operate the vehicle.

In the driver monitoring method of first embodiment, additional sensors can be provided/used to identify the person based on his/her physical characteristics such as fingerprints, facial characteristics and iris patterns.

In the driver monitoring method of first embodiment, one or more vehicle sensors can be included to receive data relating to the location, speed and/or movements of the vehicle.

In the driver monitoring method of first embodiment, the method can account for external factors that can affect pupillometry including at least one of external lighting, variation between individuals, and the mood or emotions of the person operating the vehicle.

In the driver monitoring method of first embodiment, one or more face analysis sensors can be used to detect the position of the head and facial expressions of the person operating the vehicle.

In the driver monitoring method of first embodiment, the method can trigger a response if the person operating the vehicle is distracted or is likely to become distracted beyond a specified threshold.

In a second embodiment, there is provided a driver monitoring method comprising:

providing an eye tracking system, providing one or more heart rate sensors, collecting and fusing data from said eye tracking system and the one or more heart rate sensors to obtain a value for a person's level of distraction, and further fusing data from said one or more heart rate sensors with the value for the person's level of distraction to predict if the person will experience a debilitating episode that can affect his/her ability to safely operate the vehicle.

In the driver monitoring method of second embodiment, the debilitating episode can be a result of a seizure, a stroke, a syncope, diabetes, low blood pressure, drugs, or alcohol.

In the driver monitoring method of second embodiment, the method can trigger a response if it determines that the person is or will experience a debilitating episode that can diminish his/her ability to safely operate the vehicle.

In the driver monitoring method of second embodiment, additional sensors can be provided or used to identify a person based on his/her physical characteristics such as fingerprints, facial characteristics and iris patterns.

In the driver monitoring method of second embodiment, the method can comprise recording baseline levels of activity from the eye tracking system and the one or more heart rate sensors to detect aberrations.

In the driver monitoring method of second embodiment, the method can include clinical data to predict whether the person operating the vehicle is likely to suffer a cardiac event.

In the driver monitoring method of second embodiment, one or more vehicle sensors can be included or used to collect data related to the location, speed and/or movements of the vehicle.

In the driver monitoring method of second embodiment, one or more face analysis sensors can be used or included to detect the position of the person's head as well as his/her facial expressions.

In a third embodiment, there is provided a method for analyzing a person operating a vehicle comprising using one or more computers programmed to perform operations comprising:

receiving data relating to the person's eyes and/or pupils;

receiving data relating to the person's heart rate;

performing a first fusion of data to determine and/or predict whether the person is unfit to drive because he/she is becoming distracted; and performing a second fusion of data that can include clinical data to detect and/or predict if the person will experience a debilitating episode that can affect his/her ability to safely operate the vehicle.

The method of third embodiment, can include additional operations of: receiving data relating to the position and movement of a person's head and body; and receiving data relating to the person's facial expressions.

The method of third embodiment can include the additional operation of receiving data related to location, speed and/or movement of the vehicle being operated by the person.

The method of third embodiment can analyze the output from the first fusion of data and the second fusion of data to ascertain whether the determination and/or prediction of a debilitating episode was a false positive.

The method of third embodiment can account for external factors during the first fusion of data, wherein the external factors are those which can affect the person's pupils and are selected from the group of external lighting, individual differences, and the person's mood or emotions.

BRIEF DESCRIPTION OF THE FIGURES

The summary above, as well as the following detailed description of illustrative embodiments, is better understood when read in conjunction with the appended drawings. For the purpose of illustrating the disclosure, exemplary constructions of the disclosure are shown in the drawings. However, the disclosure is not limited to specific methods and instrumentalities disclosed herein. Wherever possible, like elements have been indicated by identical numbers.

DETAILED DESCRIPTION OF THE INVENTION

Definitions

Figure 1:
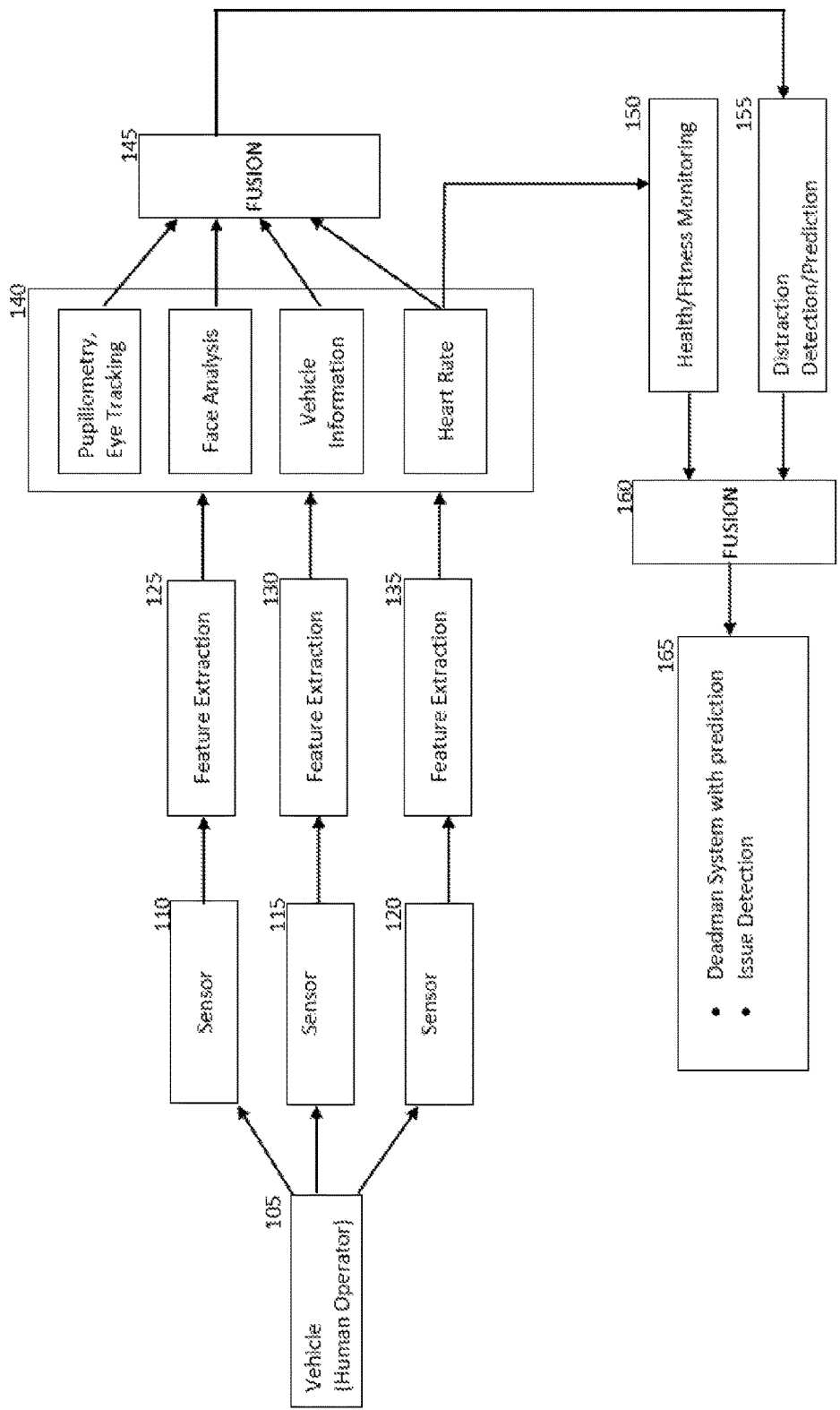
FIG. 1 is a schematic diagram of a system for pupillometry and sensor fusion for vehicle operator monitoring, according to an embodiment of the invention.

While the embodiments are described for improving road and driver safety, it is understood that the invention is not so limited and can be used to assist with other endeavors that require monitoring a person's heart and the level of distraction that he/she experiences. Other applications include, for example, using embodiments of the invention in a bus, train, aircraft or maritime vehicle and/or use to monitor the activities of individuals/employees in a work environment, a clinical or hospital setting.

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can be in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

The term "cardiac event" or "cardiovascular event" refers to any severe or acute cardiovascular condition such as a myocardial infarction, unstable angina or cardiac mortality.

The term "cognitive" refers to of, relating to, being, or involving conscious intellectual activity (such as thinking, reasoning, or remembering).

The term "cognitive distraction" refers to driver inattention, (i.e. while driving a motor vehicle, not keeping one's focus on driving). Cognitive distraction can occur when an individual's focus is not directly on the act of driving and his/her mind "wanders."

The term "cognitive overload" refers to a situation where a person or driver receives too much information or too many tasks to learners simultaneously, resulting in him/her being unable to process this information.

The term "Controller Area Network," "CAN" or "CAN bus" refers to a vehicle bus standard designed to allow microcontrollers and devices to communicate with each other in applications without a host computer.

The term "cardiac risk factor" or "risk factor" refers to a condition or habit that raises one's risk of Coronary Heart Disease (CRD). Common risk factors include familial history of stroke/heart attack, high blood pressure, cholesterol, obesity, tobacco use, lack of physical activity and diabetes.

The term "data fusion system" refers to a system that can align/integrate data sets and combine them to produce a meaningful result or conclusion.

The term "dead man's switch" or "dead man system" refers to a switch that is automatically operated if the driver of a vehicle becomes incapacitated, such as through cardiac event, loss of consciousness or death.

The term "debilitating episode" refers to an instance wherein one is unfit to drive due to a loss or impairment of cognitive function. A debilitating episode can be caused by various ailments such as stroke, low blood pressure, seizure, fatigue, diabetes and drugs/alcohol.

The term "driver state monitoring system" or "DSM" refers to a system that collects observable information about a driver in order to assess her/his capability to drive in a safe manner.

The term "fatigue" refers to tiredness resulting from mental or physical exertion or illness.

The term "fusion" or "data fusion" refers to the process of integration of multiple data and knowledge into a consistent, accurate, and useful representation.

The term "Heart rate variability" or "HRV" is the physiological phenomenon of variation in the time interval between heartbeats. It is measured by the variation in the beat-to-beat interval.

The term "High-Level Fusion" refers to the ability of a system to capture awareness and complex relations, reason over past and future events, utilize direct sensing exploitations and tacit reports, and discern the usefulness and intention of results to meet system-level goals.

The term "impairment" refers to any number of conditions that may reduce or negatively affect a driver's performance, including drowsiness, fatigue, distraction, intoxication, illness, anxiety or agitation.

The term "k-Nearest Neighbor" or "k-NN" refers to a nearest-neighbor classification object, where both distance metric ("nearest") and number of neighbors can be altered. The object classifies new observations using the predict method. The object contains the data used for training, so can compute re-substitution predictions.

The term "module" refers to a self-contained unit, such as an assembly of electronic components and associated wiring or a segment of computer software, which itself performs a defined task and can be linked with other such units to form a larger system.

The term "Multilayer Perception Neural Network" or "MLP" refers to a feedforward neural network with one or more layers between input and output layers. Feedforward means that data flows in one direction from input to output layer (forward). MLPs are widely used for pattern classification, recognition, prediction and approximation. Multi-Layer Perceptron can solve problems which are not linearly separable.

The term "myocardial infarction" refers to a heart attack which can happen when blood flow stops to a part of the heart causing damage to the heart muscle.

The term "pupillometry" refers to the measurement of pupil diameter. Pupillary responses can reflect activation of the brain allocated to cognitive tasks. For example, greater pupil dilation can be associated with increased processing in the brain.

The term "synthetic data" refers to any production data applicable to a given situation that are not obtained by direct measurement.

The term "Support Vector Machine" or "SVM" refers to supervised learning models with associated learning algorithms that analyze data used for classification and regression analysis. Given a set of training examples, each marked as belonging to one or the other of two categories, an SVM training algorithm builds a model that assigns new examples to one category or the other, making it a non-probabilistic binary linear classifier.

Other technical terms used herein have their ordinary meaning in the art that they are used, as exemplified by a variety of technical dictionaries.

Description of Preferred Embodiments

The particular values and configurations discussed in these non-limiting examples can be varied and are cited merely to illustrate at least one embodiment and are not intended to limit the scope thereof.

Distracted driving activities include things like using a cell phone, texting, and eating. In-vehicle technologies (such as driver controls, stereo systems and navigation systems) can also be sources of distraction. While any of these distractions can endanger the driver and others, text messaging ("texting") while driving is particularly dangerous because it combines both cognitive and behavioral distraction.

Eye tracking systems and pupillometry have been used to estimate cognitive load and distraction. For example, pupil diameter can change with cognitive and auditory distraction. However, real world applications to assess cognitive load and attention are challenging due to other factors that affect pupil dilation. These include individual differences, lighting, emotions and other external factors. The invention recognizes that fusing data from multiple sensors can account for these external factors. Further, the effectiveness of eye movements and pupillometry can be significantly enhanced by combining other measures such as physiological measures, steering control and lane position.

Recent studies have demonstrated the possibility of predicting cardiovascular and cerebrovascular events utilizing clinical data collected from healthy and at-risk patients. For example, see Melillo et al. (2015), "Automatic Prediction of Cardiovascular and Cerebrovascular Events Using Heart Rate Variability Analysis," PLoS ONE 10(3): e0118504. Doi:10.1371/journal.pone.0118504. Also, see Ebrahimzadeh et al. (2014), "A Novel Approach to Predict Sudden Cardiac Death (SCD) Using Nonlinear and Time-Frequency Analyses from HRV Signals," PLoS ONE 9(2): e81896. Doi.org/10.1371/journal.pone.0081896. While these methods rely on observations from healthcare professionals and are limited to clinical environments, the invention recognizes that the principles can be used in driver state monitoring.

FIG. 1 is a schematic diagram of a system for pupillometry and sensor fusion for vehicle operator monitoring, according to one aspect of the invention. The driver (human operator) 105 can turn on the system or activate it through the ignition switch of a car. In an alternative design, the system is voice activated. Multiple sensors (110, 115, 120) monitor the driver and the vehicle.

Although three sensors are illustrated (110, 115, 120), the system can include an array of various sensors for redundancy and improved robustness. For example, the system can include eye sensors, pupillometry sensors, face analysis sensors, body position sensors, body posture sensors, audio sensors, motion sensors, heart rate sensors and physiologic sensors. The sensors can monitor physiological activity of the driver including: heart/pulse rate, blood pressure, respiration rate/pattern, heart rate variability, body posture, body movement, electromyographic data, head position, head movement, eye direction, eye movement, gaze pattern/direction, eyelid opening, blink rate, eyebrow activity, pupil size, pupil activity, facial expressions, facial activity, speaking activity, speaking volume. One or more ambient light sensors can be used to account for external lighting that can affect the driver's pupils. The system can also include monitors to detect substances in the driver's system such as alcohol, drugs and/or drug metabolites. In a preferred design, the system includes one or more infrared (IR) cameras with eye tracking capability for pupillometry.

Vehicle sensors can include accelerometers, GPS sensors, motion sensors and cameras to detect obstacles and other traffic. The vehicle sensors can monitor movement of the vehicle including: vehicle speed, speed variation, erratic/irregular steering, variation in driving habits, drifting or movement within or outside of a road lane, sudden stopping, reaction times, erratic movements, incomplete or a failure to stop at intersections/stopping points and/or violations of vehicle codes/laws.

Features from the sensors can be extracted (125, 130, 135) to a module or central computer 140. In a preferred design, the sensors use one or more Controller Area Networks (CAN) to communicate with each other. The distraction detection and cardiac/health monitoring can be done in separate modules as illustrated 140. The data can then be fused 145 to yield one (or more) values or numerical representations. By fusing data from multiple sensors, the system can account for external factors that are likely to affect driver activities such as pupillometry and eye movement. For example, external lighting, physiological measures, steering control and lane position can affect the driver's pupil size and activity.

One or more algorithms can be used to weigh/adjust the value of data obtained from each sensor. A value above a certain threshold can indicate a high level of distraction. The system can activate an alert or notification upon detecting or predicting a level of distraction above a certain threshold.

The system can identify particular habits and customs of a driver so that it can predict whether the driver is likely to become distracted. Data can be collected from multiple trips/actions taken and recorded by the system. For example, the system can analyze patterns of conduct/activity presented by a driver that are associated or correlated with increased levels of distraction. A particular driver may become distracted during certain times of the day or as a result of particular activities (e.g. a phone call). The system can predict when a driver begins to display fatigued behavior and has been in a vehicle for a long period of time and/or has driven a long distance without stopping or interacting with others. In such case, the system can invoke a response to prevent the distraction and/or alert the driver.

The system can also include one or more heart rate monitors. For example, sensors on the steering wheel can detect the driver's pulse rate. Heart rate data 150 can be fused 160 with the distraction data/values 155 to determine and/or predict whether the driver is or will suffer from a cardiac event. Combining data from multiple sensors produces a more accurate indicator. A value above a certain threshold can indicate a high level of possibility of a cardiac event such as a myocardial infarction. In extreme circumstances, such as a cardiac arrest, the system can operate a "dead man system" 165. This could occur if the driver suffered a cardiac arrest but the system did not predict a cardiac event. In such circumstance, the system can invoke a response such as notifying EMS and/or causing the vehicle to decelerate and stop.

The system can also use data to determine whether the determination/prediction of a debilitating condition was caused by a false positive. A discrepancy of data from different sources can indicate a false positive. For example, data from the heart rate monitor can indicate a cardiac arrest whereas no significant distraction is detected. In this situation, the system can analyze data from multiple sensors and classifiers, including heart rate monitors and distraction detection, to identify a false positive.

The system can also detect and monitor driving patterns, for example, erratic or unnatural movements. Cameras and/or a GPS system with live updates can determine whether the vehicle is travelling at a proper speed based on road and traffic conditions. The system can also employ a series of sensors to collect related data. Cameras can also be included to monitor the body movements and optical activity of the driver as described below.

Visual Distraction

The system can detect and monitor glance pattern, mean glance duration and the duration of "eyes off road." Cameras can detect behavior such as eye-lid movement, blinking behavior and pupillometry. Further, body position and movements can also be monitored. One or more high resolution light or Infrared (IR) cameras can be used.

Manual Distraction

The system can monitor head direction, driver posture and facial expressions. Eye direction and head position can also be monitored.

Auditory Distraction

The system can monitor pupil diameter and blink frequency as indicators of auditory distraction. The system can also consider whether the driver is using an external devices (e.g. a cell phone). External sounds can also be detected and monitored.

Cognitive Distraction

Unlike visual and manual distraction, cognitive distraction can be difficult to observe from external behavior. The system can utilize pupillometry and data from other sensors to detect/predict cognitive distraction. Data can be "fused" from multiple sensors/cameras to analyze levels of cognitive distraction experienced by the driver.

Driver Fatigue

Fatigue driving occurs when the driver experiences mental and physical functional disorder, usually after prolonged periods of continuous driving. Fatigue reduces situational awareness and also affects the central nervous system and consequently mental and motor coordination. The system can analyze, for example, eye-lid movement, blinking behavior and body posture. It can detect behavior such as yawning, nodding, slouching and raising eyebrows.

Driver Heart Activity

Sensors can detect the driver's pulse rate. Heart rate can be used as a factor in predicting driver distraction. Further, heart rate data can be fused with distraction data/values to determine whether there is a likelihood that the driver is suffering a cardiac event. For example, the system can detect many symptoms that are frequently encountered during a heart attack such as pressure, tightness, pain, or a squeezing or aching sensation in the chest or arms, nausea, chest or abdominal pain, shortness of breath, cold sweat, fatigue, light headedness or dizziness. These symptoms can be "fused" with other data such as vehicle movement, body posture and pupillometry to more accurately detect/predict a cardiac event. External data can also be used in the fusion process. For example, the system can utilize clinical data related to heart rate variability (HRV) and a driver's risk factors.

Figure 2:
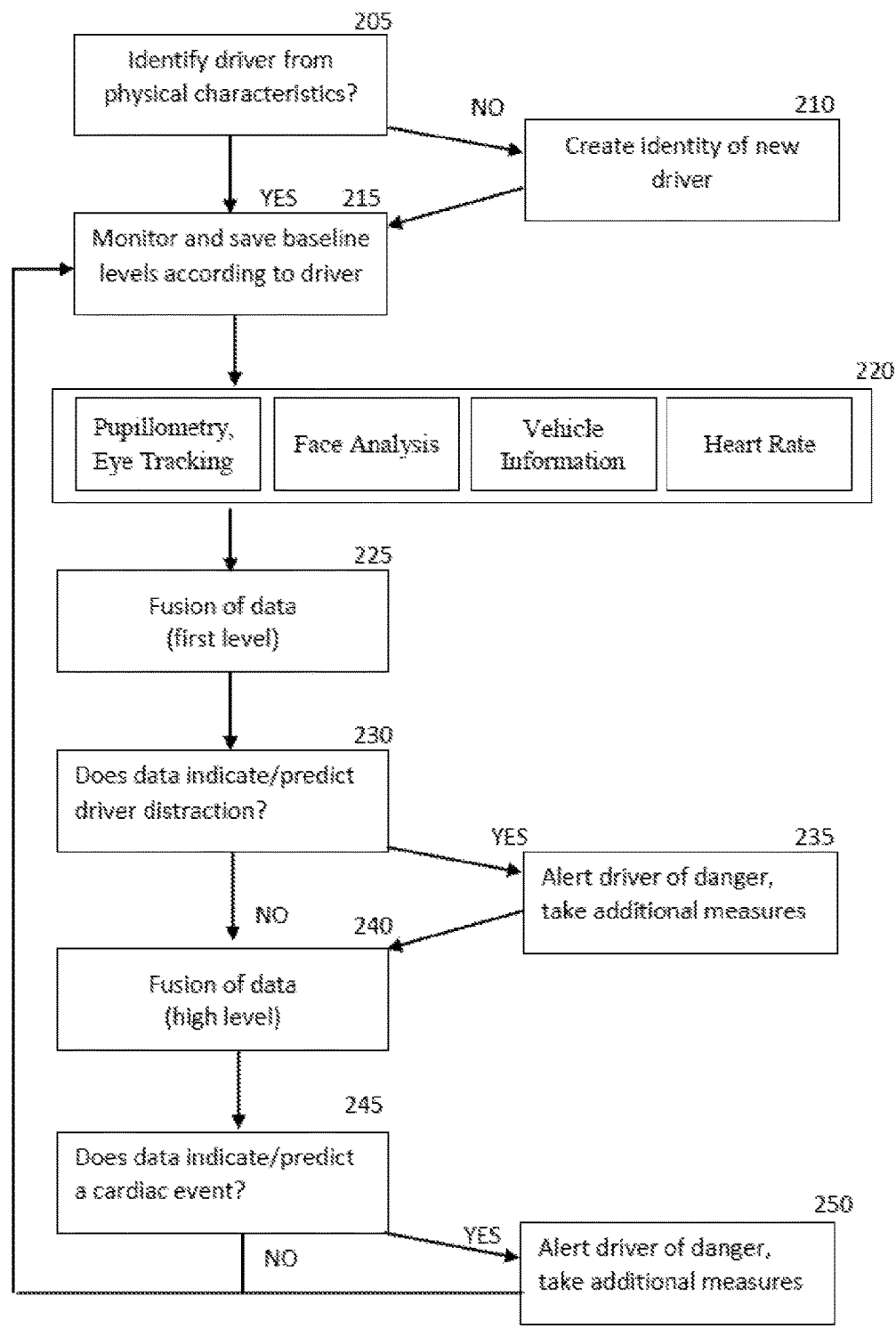
FIG. 2 is a flow chart that depicts a series of steps in the operation of an embodiment of the invention.

FIG. 2 is a flowchart of a preferred series of steps that the system uses. The system can be activated when a driver turns on the ignition switch of a vehicle (not shown). The system can begin by identifying physical characteristics of the driver as at step 205. This can include a scan of the driver's eyes and/or pupils. If the driver has previously driven the vehicle, his/her profile can be stored in the system. The driver's profile can include data related to previous incidents when he/she became distracted. The data can also include the events and circumstances that contributed to the distraction (e.g. time of day, length of trip, road conditions and presence/absence of passengers, phone calls). If the driver is new to the vehicle, then the system can create a new identity, as at step 210.

Thereafter, the system can begin monitoring the driver to establish baseline levels of activity, as at step 215. In a preferred method, the system uses one or more sensors for eye tracking and pupillometry. The sensors can be cameras capable of photographing the driver's pupils and detecting changes. The system can use another camera (or separate feature of the same camera) to analyze the driver's face and monitor, for example, his/her expressions and eyelid activity. One or more heart rate sensors can also be included. The system can also monitor vehicle information including its speed, movement, location, traffic and road conditions. This is illustrated at step 220. Further, the system can account for such things as driver mood and external lighting that can affect the activity of his/her pupils. During normal driving, the system can use sensors and/or cameras to observe and record baseline levels.

The data can then be fused to yield one (or more) values or numerical representations as at step 225. This can be referred to as a "first" or "low" level of fusion because it combines several sources of raw data to produce new raw data. However, the fused data is more informative and synthetic than the original inputs.

The baseline levels can be used to determine whether data is aberrant and if so, whether the driver is experiencing a high level of distraction or cognitive overload as at step 230. In another embodiment, the system can predict if a driver will become distracted. The system can include driver habits and past experiences to make such predictions. For example, a particular driver may tend to lose cognitive abilities after 30 minutes of driving in slow traffic, particularly in evening hours. The system can store and use this data along with sensor data in its analysis.

A value above a certain threshold can indicate a high level of distraction. If distracted, the system alert the driver, as at step 235. The system can also be programed to take a responsive action by, for example, activating an audio system. Other potential actions can include adjusting the interior lighting and/or temperature, turning on or adjusting the volume of the stereo, notifying a parent or guardian and/or contacting law enforcement or a municipal authority.

The system can also monitor the heart rate of a driver. This can be accomplished by, for example, sensors in the steering wheel to detect the driver's pulse rate, also at step 220. The system can maintain baseline levels of heart activity for individual drivers under the premise that levels can increase due to stress or other external factors.

The system can fuse the heart rate data with values/data collected from the other sensors, as at step 240. This can be referred to as a "second" or "high" level of fusion because it combines new raw data with external data. External data can include data collected from clinical studies related to cardiac events. For example, studies have demonstrated that Heart Rate Variability (HRV) analysis can be used to predict cardiovascular and cerebrovascular events. External clinical data related to HRV can be included to predict whether the person is likely to suffer a cardiac event. The system can also include personal risk factors and one's medical history to better predict whether the person is likely to suffer a cardiac event.

A value above a certain threshold can indicate and/or predict the possibility of a cardiac event such as a myocardial infarction 245. In such an event, the system can take one or more actions, as at step 250. For example, the system can alert the driver to safely stop the vehicle and contact authorities. It can also contact medical and/or EMS (Emergency Medical Services) authorities directly as well as activate a "kill switch" under extreme circumstances.

By fusing inputs from different sensor and establishing an individual's history, the disclosed invention can accurately classify whether a driver is distracted or subject to cognitive distraction/overload. Further, it can monitor and predict cardiac events. In normal operation, the system will continuously monitor the driver and can incorporate driving time, distance and road conditions as factors in determining the driver's condition.

Figure 3:
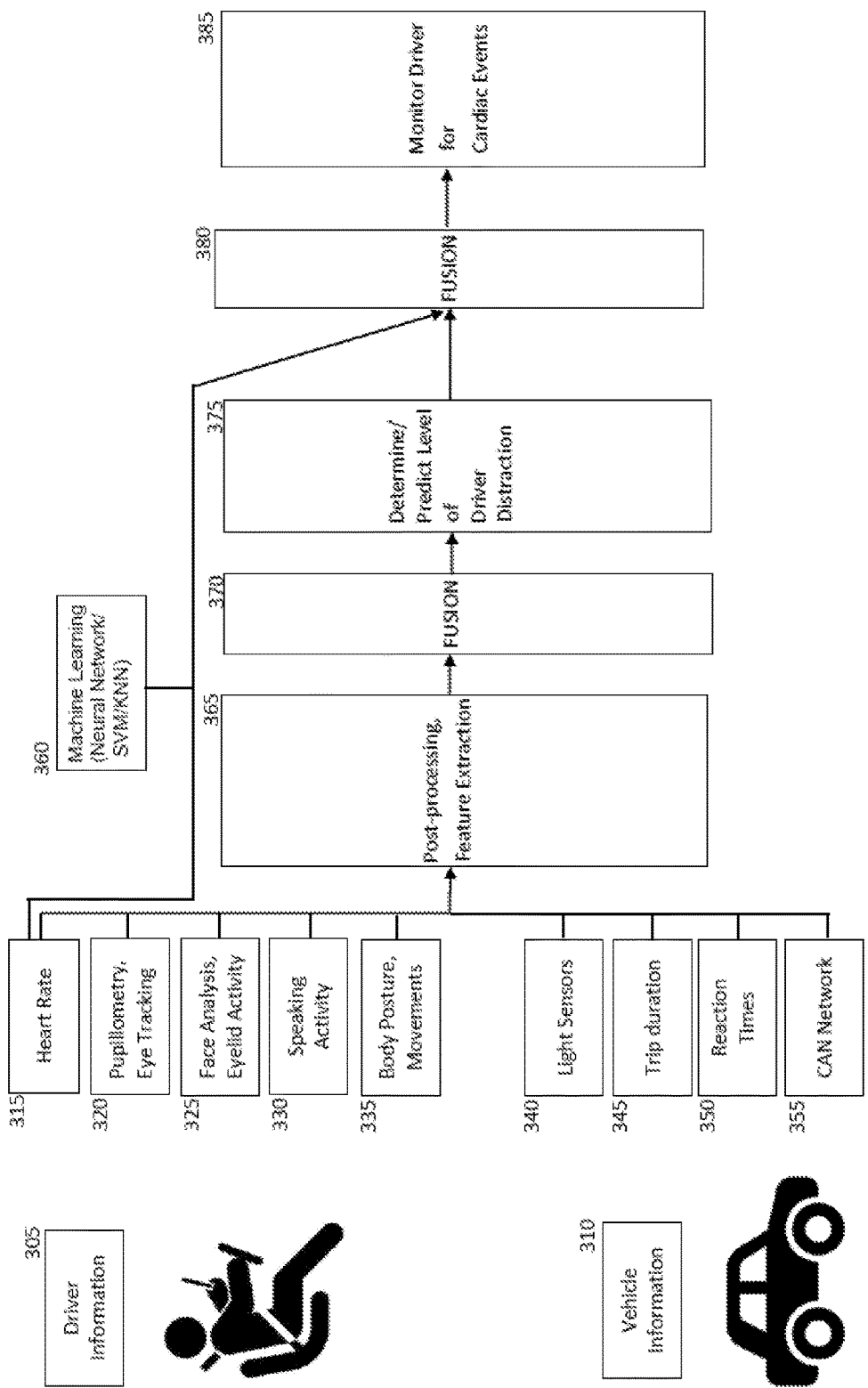
FIG. 3 is a schematic diagram that depicts sensors and modules of an embodiment of the invention.

FIG. 3 is a schematic diagram that depicts some sensors and modules of the invention. In a preferred embodiment, the invention includes sensors that detect information on the driver 305 and sensors that detect vehicle information 310. Sensors can monitor the driver's heart rate and HRV 315. An eye tracking system can include one or more sensors to monitor pupillometry, eye movement and eye activity 320. Other sensors monitor the face and eyelids 325, speaking activity and volume 330 as well as the driver's posture and movements 335. Vehicle sensors can monitor ambient light 340, trip duration 345 and driver reaction times 350. A Controller Area Network (CAN bus) 355 can be included to allow microcontrollers and devices to communicate with each other.

Data from the sensors can undergo post-processing, feature extraction 365 and fusion 370 to determine and/or predict the level of distraction that a driver is experiencing 375. The system can also make predictions about a driver's likelihood of becoming distracted based on his/her particularly habits and characteristics. Further, the system can account for external factors (e.g. light, driving and road conditions) that can affect the driver's pupils, eyes and body movement. For example, external lighting, road conditions and environmental stress can affect the driver's pupil size and activity.

Heart rate data can be fused 380 with the distraction data/values to monitor the driver's cardiac activity and determine/predict a debilitating episode or cardiac event 385. As described, the system can incorporate external clinical data from both healthy people and others with heart disease and high risk of cardiac episode. The system can classify a person by Support Vector Machine (SVM), k-Nearest Neighbor (k-NN) and/or Multilayer Perception Neural Network (MLP) as at step 360.

Figure 4:
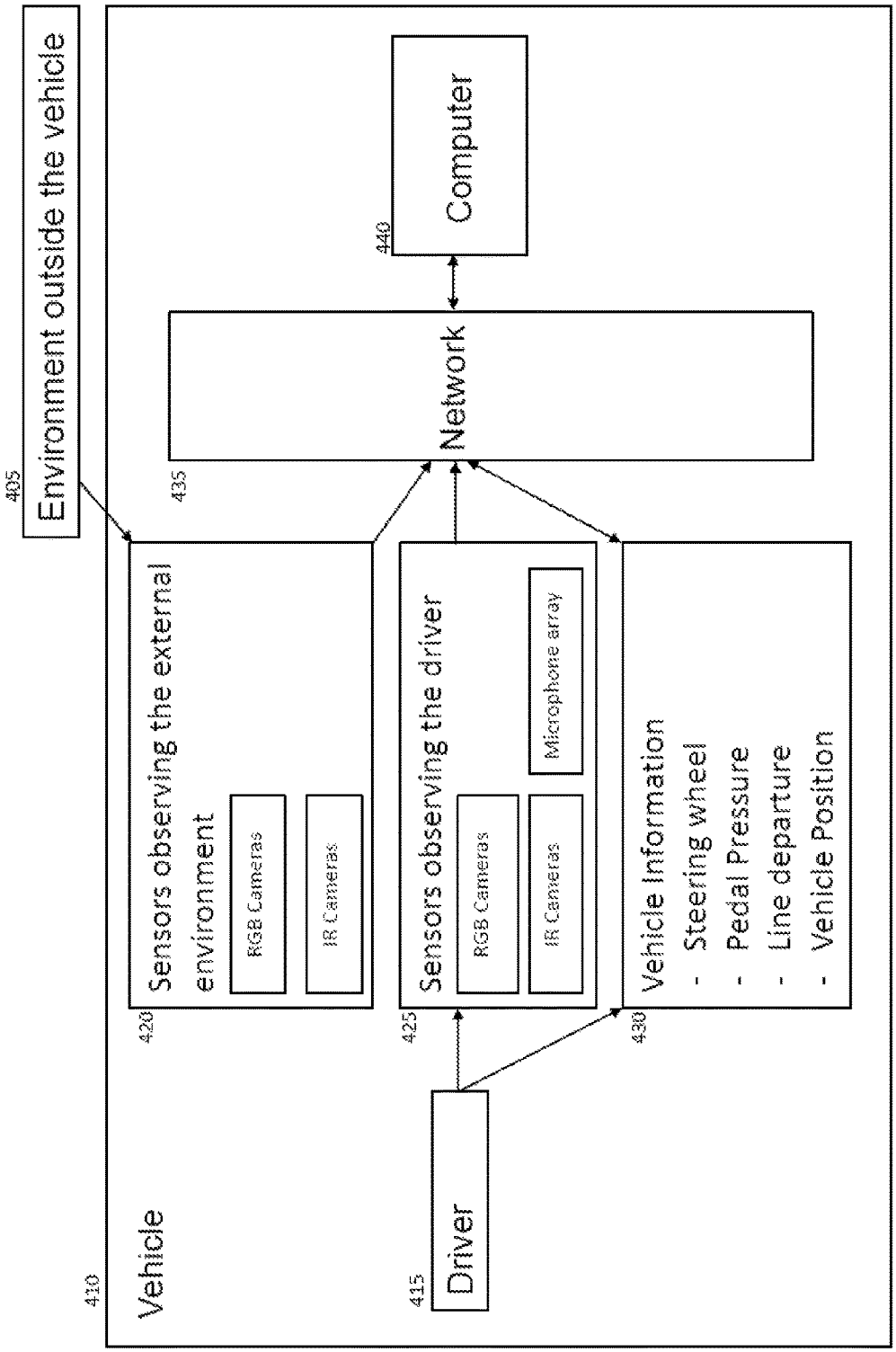
FIG. 4 is a schematic diagram that depicts the hardware of an embodiment of the invention.

FIG. 4 is a schematic diagram that depicts a preferred organization of the hardware of the system. Both the driver 415 and the external environment 405 are monitored. The vehicle 410 includes sensors that monitor the external environment 420 along with sensors that observe the driver 425 and vehicle information 430. The system can include both color (RGB) and infrared (IR) cameras along with a microphone array.

In a preferred design, vehicle information 430 is compiled from several sensors. The steering wheel can include sensors to detect the driver's pulse rate, hand position, grip pressure and steering actions. Pedal pressure (i.e. accelerator and brake) can also be detected and similarly monitored. Further, the system can monitor movements of the vehicle and detect sporadic or irregular movements that can indicate reduced cognitive abilities.

The sensors relay information to a network 435 and then to a computer 440. The computer can store and analyze the data.

Working Example

Detection and Monitoring an Automobile Driver's Health and Level of Attention

I. Driver Identification

The system can identify a driver based on, for example, the driver's eyes and other physical characteristics. Face and/or voice recognition and/or fingerprints can also be used. The system can save information on each driver of a vehicle. Stored information can include past driving habits, past episodes of diminished cognitive function (and related data) as well as health information such as HRV. Thus, when a driver sits in the driver seat, the system can identify a driver and access data for him/her. If it identifies a new driver, the system can open a new file to begin collecting baseline data on that individual.

II. Establishment of Baseline Habits and Characteristics

The system can detect and analyze a driver's characteristics during normal driving. This information can be saved/recorded on the system or remotely, for example, on cloud storage. The baseline characteristics can thereafter be used to detect irregular driving patterns that can otherwise be attributed to distracted driving. The system can also detect normal cardiac activity for the particular driver. Thus, the system can identify irregular cardiac activity, such as increased or sporadic heart rate. This, along with clinical data, can assist in detecting and/or predicting a cardiac event such as a myocardial infarction.

III. Analysis of the Driver's Level of Distraction

GPS and Detection of Location/Movement

The system can use external cameras and incorporate data and updates from a GPS (Global Positioning System) in a vehicle to account for the location of the vehicle, speed limits and street characteristics. Traffic and adverse weather conditions can be incorporated with live updates. This can help the system determine whether the car is being driven at a normal speed based on the driver's habits and road conditions. Irregular speeds and movements can be a factor considered in determining whether the driver is distracted or experiencing a cardiac event. Irregular Driving patterns can include:

1) Inappropriate (often slow) or irregular speed for a particular stretch of road;
2) Irregular steering and/or overcorrection of steering;
3) Swerving or erratic movements; and/or
4) Slow or delayed reaction times.

Eye Monitoring

The system can use one or more cameras to monitor the eyes of the driver. The duration of time that the driver's eyes are not directed to the road ("eyes off road") is one factor that can be considered. This is analyzed by considering the direction of the driver's head and body position as well as his/her eye direction, focus and glance pattern. Increased cognitive load can be demonstrated by:

1) Longer fixations;
2) Gazing toward the center of the field of view; and/or
3) Less frequent glances at mirrors and/or gauges.

Driver Posture and Activity

One or more cameras can be directed to the driver's head and upper body to monitor his/her posture and level of activity. Facial behavior (e.g. expressions and movement) can also be detected and monitored. Aberrations of baseline behavior can be indicative of, for example, a high level of distraction, fatigue or drowsiness.

Pupillometry

Pupil Diameter can indicate cognitive and auditory distraction. The system can account for the driver's typical pupil responses as well as individual differences, lighting, emotions and other external factors by "fusing" data from multiple sensors. That is, the effectiveness of eye movements and pupillometry can be significantly enhanced by combining other measures such as external lighting, physiological measures, steering control and lane position.

IV. Fusion of Data to Determine and Predict the Level of Distraction

The system can use one or more algorithms to "fuse" the data collected by the sensors and cameras. The system can produce one or more values to gauge the level of distraction being experienced by the driver. The system can also predict whether the driver will become distracted based on his/her previous actions and responses. Distraction beyond a specific level (e.g. cognitive overload) can indicate that a driver is too distracted to drive safely. If the driver is distracted beyond this threshold (or is likely to become distracted beyond the threshold), the system can alert the driver and/or take another appropriate action.

V. Analysis of the Driver's Heart Activity

The system can use one or more sensors to monitor the heart rate and Heart Rate Variability (HRV) of an individual. The system can also detect normal cardiac function as well as identify abnormal activity, such as an increased or sporadic heart rate. This, along with other data, can assist in detecting or predicting the occurrence of a cardiac event such as a myocardial infarction. It is also possible to use the system to monitor for stroke, seizure or other condition that can affect a driver's ability to safely operate a motor vehicle.

VI. Fusion of Data to Monitor the Driver for Cardiac Events

The system can use one or more algorithms to "fuse" external clinical data with the data collected by the sensors and cameras. The system can produce one or more values to determine the likelihood that a driver is or will experience a cardiac event. This high-level fusion can include HRV data from both healthy individuals and individuals who have suffered a cardiac event such as a myocardial infarction or sudden cardiac death (SCD). If the system determines that the driver is experiencing (or is likely to experience) a cardiac event, the system can respond appropriately. For example, the system can alert the driver and limit additional driving and/or assist in contacting medical professionals.

It is also possible for the system to monitor a driver for impairment due to drugs or alcohol or other condition such as epileptic seizure, loss of consciousness (e.g. fainting) and/or diabetic incidents that can affect a driver's ability to safely operate a motor vehicle. For example, the system can monitor and detect the driver's loss of cognitive function due to alcohol. The system can detect that the driver is distracted without attributing the cause to drugs or alcohol. In an alternative design, the system can include sensors to detect alcohol and/or drugs and related metabolites.

It will be appreciated that variations of the above disclosed and other features and functions, or alternatives thereof, may be combined into other systems or applications. Also, various unforeseen or unanticipated alternatives, modifications, variations or improvements therein may be subsequently made by those skilled in the art which are also intended to be encompassed by the following claims.

Although embodiments of the current disclosure have been described comprehensively, in considerable detail to cover the possible aspects, those skilled in the art would recognize that other versions of the disclosure are also possible.

What is claimed is:

1. A driver monitoring system comprising:
   a. an eye tracking system;
   b. one or more heart rate sensors; and
   c. one or more vehicle sensors configured to receive data related to a variation in a driving habit of a person operating a vehicle,
   wherein the driver monitoring system is configured to collect data from the eye tracking system, the one or more heart rate sensors and the one or more vehicle sensors to record the data to establish baseline levels of activity for the person operating the vehicle;
   wherein the driver monitoring system is configured to fuse the data to determine a level of distraction being experienced by the person operating the vehicle;
   wherein the driver monitoring system is configured to include personal risk factors and medical history of the person operating the vehicle; and
   wherein the driver monitoring system is further configured to predict whether the person operating the vehicle will suffer a debilitating episode that can diminish his/her ability to safely operate the vehicle based on the fused data, the personal risk factors and the medical history of the person operating the vehicle.

2. The driver monitoring system of claim 1, wherein additional sensors are included to identify the person operating the vehicle based on his/her physical characteristics selected from the group consisting of fingerprints, facial characteristics, and iris patterns.

3. The driver monitoring system of claim 1, wherein one or more additional vehicle sensors are included to receive data relating to a location, speed, and/or movements of the vehicle.

4. The driver monitoring system of claim 1, wherein the driver monitoring system is configured to account for external factors that affect pupillometry including at least one of external lighting, variation between individuals, and the mood or emotions of the person operating the vehicle.

5. The driver monitoring system of claim 1, wherein one or more face analysis sensors are included to detect a position of the head and facial expressions of the person operating the vehicle.

6. The driver monitoring system of claim 1, wherein the driver monitoring system is configured to trigger a response if the person operating the vehicle is distracted or is likely to become distracted beyond a specified threshold.

7. The driver monitoring system of claim 1, wherein the data related to the variation in the driving habit is used to establish a baseline to detect irregular driving patterns attributed to distracted driving.

8. The driver monitoring system of claim 1, wherein the driver monitoring system is configured to incorporate external clinical data from both healthy people and others with heart disease and high risk of cardiac episode; and wherein the driver monitoring system is further configured to classify a person by machine learning.

9. A driver monitoring system comprising:
   a. an eye tracking system;
   b. one or more heart rate sensors; and
   c. one or more vehicle sensors configured to receive data related to a variation in a driving habit of a person operating a vehicle,
   wherein the driver monitoring system is configured to collect and fuse data from said eye tracking system and the one or more vehicle sensors to obtain a value for the person's level of distraction, and
   wherein the driver monitoring system is configured to fuse data from said one or more heart rate sensors with the value for the person's level of distraction, personal risk factors and medical history of the person operating the vehicle
   to predict if the person will experience a debilitating episode that can affect his/her ability to safely operate the vehicle.

10. The driver monitoring system of claim 9, wherein the debilitating episode is a result of a seizure, a stroke, a syncope, diabetes, low blood pressure, drugs, or alcohol.

11. The driver monitoring system of claim 9, wherein the driver monitoring system is configured to trigger a response if the driver monitoring system determines that the person is experiencing or will experience the debilitating episode that can diminish his/her ability to safely operate the vehicle.

12. The driver monitoring system of claim 9, wherein additional sensors are included to identify the person based on his/her physical characteristics selected from the group consisting of fingerprints, facial characteristics and iris patterns.

13. The driver monitoring system of claim 9, wherein the driver monitoring system is configured to record baseline levels of activity from the eye tracking system and the one or more heart rate sensors to detect aberrations.

14. The driver monitoring system of claim 9, wherein the driver monitoring system is configured to include clinical data to predict whether the person is likely to suffer a cardiac event.

15. The driver monitoring system of claim 9, wherein one or more additional vehicle sensors are included to collect data related to a location, speed, and/or movements of the vehicle.

16. The driver monitoring system of claim 9, wherein one or more face analysis sensors are included to detect a position of the person's head as well as his/her facial expressions.

17. The driver monitoring system of claim 9, wherein the data related to the variation in the driving habit is used to establish a baseline to detect irregular driving patterns attributed to distracted driving.

18. A system for analyzing a person operating a vehicle comprising one or more computers programmed to perform operations comprising:
  a. receiving data relating to the person's eyes and/or pupils;
  b. receiving data relating to the person's heart rate;
  c. receiving data relating to a variation in a driving habit of the person operating the vehicle;
  d. performing a first fusion of data comprising fusing the data relating to the person's eyes and/or pupils with the data relating to the variation in the driving habit of the person operating the vehicle and the data relating to the person's heart to determine and/or predict whether the person is unfit to drive because he/she is becoming distracted;
  e. including personal risk factors and medical history of the person operating the vehicle; and
  f. performing a second fusion of data comprising fusing output of the first fusion with the personal risk factors and the medical history of the person operating the vehicle to detect and/or predict if the person will experience a debilitating episode that can affect his/her ability to safely operate the vehicle.

19. The system of claim 18, further comprising additional operations of:
  receiving data relating to a position and movement of the person's head and body; and
  receiving data relating to the person's facial expressions.

20. The system of claim 18, including an additional operation of receiving data related to location, speed and/or movement of the vehicle being operated by the person.

21. The system of claim 18, wherein the system is configured to analyze output from the first fusion of data and the second fusion of data to ascertain whether the determination and/or prediction of the debilitating episode was a false positive.

22. The system of claim 18, wherein the system is configured to account for external factors during the first fusion of data, wherein the external factors are those which can affect the person's pupils and are selected from a group consisting of external lighting, individual differences, and the person's mood or emotions.

23. The system of claim 18, wherein the data relating to the variation in the driving habit is used to establish a baseline to detect irregular driving patterns attributed to distracted driving.

24. A driver monitoring method comprising:
  providing an eye tracking system;
  providing one or more heart rate sensors; and
  providing one or more vehicle sensors configured to receive data related to a variation in a driving habit of a person operating a vehicle;
  collecting and fusing data from the eye tracking system, the one or more vehicle sensors and the one or more heart rate sensors to obtain a value for the person's level of distraction, including personal risk factors and medical history of the person operating the vehicle; and
  further fusing data from the one or more heart rate sensors, the personal risk factors and the medical history of the person operating the vehicle, with the value for the person's level of distraction to predict if the person will experience a debilitating episode that can affect his/her ability to safely operate the vehicle.

25. The driver monitoring method of claim 24, wherein the data related to the variation in the driving habit is used to establish a baseline to detect irregular driving patterns attributed to distracted driving.

26. A method for analyzing a person operating a vehicle comprising:
  using one or more computers programmed to perform operations comprising:
  receiving data relating to a person's eyes and/or pupils;
  receiving data relating to a person's heart rate;
  receiving data relating to a variation in a driving habit of the person operating the vehicle;
  performing a first fusion of the data relating to a person's eyes and/or pupils, the data relating to the person's heart rate and the data relating to the variation in the driving habit of the person operating the vehicle to determine and/or predict whether the person is unfit to drive because he/she is becoming distracted; and
  performing a second fusion of data that includes fusing output of the first fusion with personal risk factors and medical history of the person operating the vehicle to detect and/or predict if the person will experience a debilitating episode that can affect his/her ability to safely operate the vehicle.

27. The method for analyzing a person operating a vehicle of claim 26, wherein the data relating to the variation in the driving habit is used to establish a baseline to detect irregular driving patterns attributed to distracted driving.

* * * * *